(12) United States Patent
Naik et al.

(10) Patent No.: US 11,715,559 B2
(45) Date of Patent: Aug. 1, 2023

(54) METHODS AND APPARATUS OF MAINTENANCE SCHEDULING IN AUTOMATED TESTING OVER A PLANNING PERIOD

(71) Applicant: Siemens Healthcare Diagnostics Inc., Tarrytown, NY (US)

(72) Inventors: Sandeep M. Naik, Bridgewater, NJ (US); Micheal Heydlauf, Cary, NC (US); Ahmet Tuysuzoglu, Jersey City, NJ (US); Yue Zhang, Jersey City, NJ (US); Luxi Zheng, Cary, NC (US); Jeffrey Hoffman, Lebanon, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/597,421

(22) PCT Filed: Jun. 8, 2020

(86) PCT No.: PCT/US2020/036627
§ 371 (c)(1),
(2) Date: Jan. 5, 2022

(87) PCT Pub. No.: WO2021/015872
PCT Pub. Date: Jan. 28, 2021

(65) Prior Publication Data
US 2022/0208364 A1      Jun. 30, 2022

Related U.S. Application Data

(60) Provisional application No. 62/976,072, filed on Feb. 13, 2020, provisional application No. 62/877,887, filed on Jul. 24, 2019.

(51) Int. Cl.
*G16H 40/40*      (2018.01)
*G06Q 10/10*      (2012.01)
(Continued)

(52) U.S. Cl.
CPC ......... *G16H 40/40* (2018.01); *G06Q 10/1097* (2013.01); *G06Q 10/20* (2013.01)

(58) Field of Classification Search
CPC ..... G16H 40/40; G06Q 10/1097; G06Q 10/20
See application file for complete search history.

(56) References Cited

U.S. PATENT DOCUMENTS 6,912,481 B2      6/2005   Breunissen et al.
8,560,368 B1     10/2013   Maity et al.
(Continued)

FOREIGN PATENT DOCUMENTS

CN         1341174 A    *   3/2002    ............. D05B 11/00
WO       2015171581          11/2015
(Continued)

OTHER PUBLICATIONS

International Search Report for PCT/US2020/036627 dated Sep. 2, 2020.
(Continued)

*Primary Examiner* — Tuyen K Vo (57) ABSTRACT

Methods of scheduling maintenance on a plurality of automated testing apparatus and possibly also on ancillary test processing apparatus are provided. The methods include inputting identification data on the plurality of automated testing apparatus to be maintained, inputting maintenance requirement data for the maintenance of each of the apparatus, inputting demand constraint data, operating on the identification data, maintenance requirement data, and demand constraint data using an optimization program, such as mixed integer linear programming (MILP), subject to demand constraints and at least one objective, and outputting an optimized maintenance schedule for a planning period. Systems and apparatus configured to carry out the methods are also provided, as are other aspects.

26 Claims, 2 Drawing Sheets (51) Int. Cl.
  *G06Q 10/00*      (2012.01)
  *G06Q 10/1093*    (2023.01)
  *G06Q 10/20*      (2023.01)

(56) References Cited

U.S. PATENT DOCUMENTS

| | | | |
|---|---|---|---|
| 8,854,226 B2 | 10/2014 | Wilson | |
| 9,843,795 B1* | 12/2017 | Scherer | H04N 17/002 |
| 9,959,514 B2 | 5/2018 | Phan et al. | |
| 9,977,787 B2 | 5/2018 | Zhou et al. | |
| 10,037,502 B2 | 7/2018 | Wang et al. | |
| 10,303,508 B2 | 5/2019 | Vaish et al. | |
| 10,373,087 B1* | 8/2019 | Yang | G06Q 10/06315 |
| 2003/0139665 A1* | 7/2003 | Takayama | G16H 40/20 600/407 |
| 2004/0181368 A1 | 9/2004 | Breunissen et al. | |
| 2007/0294121 A1* | 12/2007 | Galt | B22D 17/32 705/7.12 |
| 2008/0040176 A1* | 2/2008 | Ehling | G06Q 30/012 705/302 |
| 2008/0133178 A1* | 6/2008 | Byrne | G05B 23/0283 702/184 |
| 2009/0164490 A1* | 6/2009 | Wininger | G06Q 10/06 715/705 |
| 2010/0318970 A1* | 12/2010 | Grechanik | G06Q 10/06 717/124 |
| 2013/0290135 A1* | 10/2013 | Borza | G06Q 30/0611 705/26.4 |
| 2015/0051938 A1 | 2/2015 | Li et al. | |
| 2015/0058270 A1 | 2/2015 | Kawata et al. | |
| 2017/0083822 A1* | 3/2017 | Adendorff | G06F 11/0793 |
| 2017/0091718 A1* | 3/2017 | Bullock | G06Q 50/02 |
| 2019/0195292 A1* | 6/2019 | Pan | F16D 48/06 |
| 2020/0301408 A1* | 9/2020 | Elbsat | G06N 3/04 |
| 2020/0411176 A1* | 12/2020 | Hadorn | G06N 7/005 |
| 2021/0042708 A1* | 2/2021 | Gardiner | G06Q 30/0284 |

FOREIGN PATENT DOCUMENTS

| | | |
|---|---|---|
| WO | 2015179370 | 11/2015 |
| WO | 2017083678 | 5/2017 |
| WO | 2018022351 | 2/2018 |
| WO | 2018022474 | 2/2018 |
| WO | 2018099859 | 6/2018 |
| WO | 2019156828 | 8/2019 |
| WO | 2019177724 | 9/2019 |

OTHER PUBLICATIONS

Miller Mark; "Principles of Medical Device Maintenance Automation"; Accuracy Malters; Sep. 2015; pp. 1-3.

WHO; "Consultation on Technical and Operational Recommendations for Clinical Laboratory Testing Harmonization and Standardization", Helping to Expand Sustainable Quality Testing to Improve the Care and Treatment of People Infecte with and Affected by HIV/AIDS, TB and Malaria; Jan. 2008; pp. 1-20.

Georgiadis Georgios P. et al; "Optimization-Based Scheduling for the Process Industries: From Theory to Real-Life Industrial Applications"; Processes, 2019, 7,438; doi:10.3390/pr7070438, pp. 1-35.

Boland et al., "Scheduling ar maintenance jobs in a network to maximize total flow over time", Discrete Applied Mathematics, vol. 163:34-53, (2014).

* cited by examiner

METHODS AND APPARATUS OF MAINTENANCE SCHEDULING IN AUTOMATED TESTING OVER A PLANNING PERIOD

RELATED APPLICATION

The present disclosure is related to U.S. Provisional Patent Application 62/877,887 filed on Jul. 24, 2019, entitled "Methods And Apparatus Of Maintenance Scheduling In Automated Testing."

FIELD

The present disclosure relates to methods and apparatus configured to schedule maintenance in automated testing apparatus.

BACKGROUND

Automated testing apparatus for medical applications such as clinical chemical analyzers and immunoassay instruments and ancillary test processing apparatus, such as centrifuges, decappers, aliquoters, sealers, quality check modules, and the like, may include the use of robotics or other automated or mechanical components. The automated testing apparatus are used to test and/or process a biological liquid (otherwise referred to herein as a "specimen") such as blood, blood components such as serum or plasma, urine, cerebral-spinal fluid, and the like. For example, the automated testing equipment may function to test for the presence of and/or the concentration of an analyte or constituent in the specimen. Such automated testing apparatus and ancillary test processing apparatus are complex and from time to time may experience breakdowns.

In an effort to prevent or reduce such breakdowns, routine maintenance is attempted to be implemented to maximize the possibility that such automated testing apparatus and ancillary test processing apparatus will continue to function as intended.

Accordingly, methods and apparatus that may improve the ability to maintain such automated testing apparatus and ancillary test processing apparatus are sought after.

SUMMARY

In one method embodiment, a method of scheduling maintenance on a plurality of automated testing apparatus is provided. The method includes inputting identification data on the plurality of automated testing apparatus to be maintained; inputting maintenance requirement data for maintenance of each of the plurality of automated testing apparatus; inputting demand constraint data; operating on the identification data, maintenance requirement data, and demand constraint data on a processor using an optimization program subject to demand constraints and at least one objective; and outputting a maintenance schedule for a defined period of time (e.g., over a planning period).

In an apparatus embodiment, a maintenance scheduler apparatus is provided. The maintenance scheduler apparatus includes a local data server including: local memory configured to store an identification database, a maintenance requirement database, and a demand constraint database; an optimization server configured to communicate with the local data server, the optimization server further comprising: a server memory configured to store: a compilation of identification data on a plurality of automated testing apparatus to be maintained, maintenance requirement data for maintenance of each of the plurality of automated testing apparatus, and demand constraint data in an optimization database; and an optimization program executable on the optimization server subject to demand constraints and at least one objective to generate an optimized maintenance schedule for the plurality of automated testing apparatus.

In another method embodiment, a method of scheduling maintenance on a plurality of automated testing apparatus is provided. The method of scheduling maintenance includes receiving into an identification database in local memory of a local data server, identification data on the plurality of automated testing apparatus to be maintained, wherein the identification data comprises model, serial number, asset number, or other identifier; receiving into a maintenance requirement database in local memory of the local data server, maintenance requirement data for maintenance of each of the plurality of automated testing apparatus, wherein the maintenance requirement data comprises: data on what maintenance item is to be performed on the plurality of automated testing apparatus, frequency data of the maintenance item on the plurality of automated testing apparatus, and certification requirement data for personnel who are to perform the maintenance item; receiving demand constraint data into a demand constraints database in local memory of the local data server, the demand constraint data comprising personnel availability data; communicating the identification data, the maintenance requirement data, and the demand constraint data to an optimization server; operating on the identification data, the maintenance requirement data, and the demand constraint data on the optimization server using an optimization program comprising mixed integer linear programming subject to demand constraints and at least one objective; outputting from the optimization server to the local data server an optimized maintenance schedule for a defined period of time; and outputting the optimized maintenance schedule from one or more of a local data server, from one or more of the plurality of automated testing apparatus, or from middleware.

Still other aspects, features, and advantages of the present disclosure may be readily apparent from the following detailed description illustrating a number of example embodiments. The present invention may also be capable of different embodiments, and its several details may be modified in various respects, all without departing from the scope of the present disclosure. Accordingly, the disclosure is to cover all modifications, equivalents, and alternatives falling within the scope of the disclosure as defined in the claims.

DETAILED DESCRIPTION

In view of the need for preventative maintenance, when there is a large number of such automated testing apparatus and possibly ancillary test processing apparatus, such as located in a large lab, that are in need of being maintained (such as tens to even hundreds of such apparatus), it becomes a daunting task to efficiently manage the breadth of maintenance events thereon, and it may not be possible to do so at all.

The present disclosure is directed at providing apparatus and methods configured and operable to provide an optimized maintenance schedule for a plurality of automated testing apparatus, and possibly combined with related ancillary test processing apparatus, over a defined period of time (e.g., over a planning period). The output of the apparatus and method is a detailed and optimized maintenance schedule that can be implemented over a defined period of time (e.g., over the planning period), such as per shift, per day, per week, or even per month, for example. The optimized maintenance schedule may further be provided over any other defined period of time, and may include specific maintenance instructions per each piece of automated testing apparatus and possibly related ancillary test processing apparatus. Thus, an optimized maintenance schedule may be produced providing instructions regarding maintenance for each piece of automated testing apparatus, and, if desired, for related ancillary test processing apparatus, that may be communicated thereto. For example, for each such apparatus, a "maintenance window alert" may be provided to the personnel in advance, as part of the optimized maintenance schedule. This alert may be communicated as a pop-up or in another suitable mode or medium at one or more automated testing apparatus and possibly related ancillary test processing apparatus that have a local computer and suitable peripheral (e.g., display) coupled thereto or interconnected therewith.

In particular, the detailed and optimized maintenance schedule may include: 1) a listing of what the maintenance items are to be conducted (e.g., what type of maintenance and on what apparatus); 2) the optimized maintenance window (e.g., one or more time periods) when the maintenance should take place; and 3) who (e.g., what personnel) should accomplish the maintenance item(s).

In some embodiments, the cost of each personnel and the qualification level (e.g., certification level) required for each maintenance item (task) may be considered. Optionally, a communication of how the maintenance should take place, including a list of maintenance steps, can be provided as an output, which can be followed by the personnel undertaking the maintenance. The list of maintenance steps may be communicated along with a maintenance alert to one or more of the one or more automated testing apparatus and possibly related ancillary test processing apparatus.

As a result, malfunction of the automated testing apparatus, and if desired, the related ancillary test processing apparatus, can be minimized or avoided through conducting substantially on-time maintenance to each piece of automated testing apparatus, and, if desired, the related ancillary test processing apparatus. Furthermore, implementing the apparatus and methods of scheduling maintenance of the automated testing apparatus and possibly related ancillary test processing apparatus can have one or more further advantages of:

minimizing overall testing cost,
  avoiding excessive repair downtime,
  reducing extra labor costs due to overtime for unnecessarily-urgent repairs,
  ensuring compliance with laboratory regulations,
  maximizing system availability to produce on-time test results,
  reducing mean time to repair by having the right set of components (spare parts) available (e.g., pre-ordered) in advance, to be replaced during the maintenance,
  ability to schedule maintenance at opportune times, such as when the automated testing apparatus or related ancillary test processing apparatus is not in use or at times of lower usage,
  ability to schedule maintenance at times when a qualified personnel is available to perform the maintenance item, and
  ability to schedule maintenance at times when the automated testing apparatus is not required for urgent testing.

In view of the foregoing, one or more embodiments of the disclosure provide methods and apparatus configured and operable to provide an optimized maintenance schedule, wherein the optimized maintenance schedule can then be carried out to accomplish maintenance of a plurality of automated testing apparatus and, if desired, on related ancillary test processing apparatus.

These and other aspects and features of embodiments of the disclosure will be described with reference to FIGS. 1-2 herein.

Figure 1:
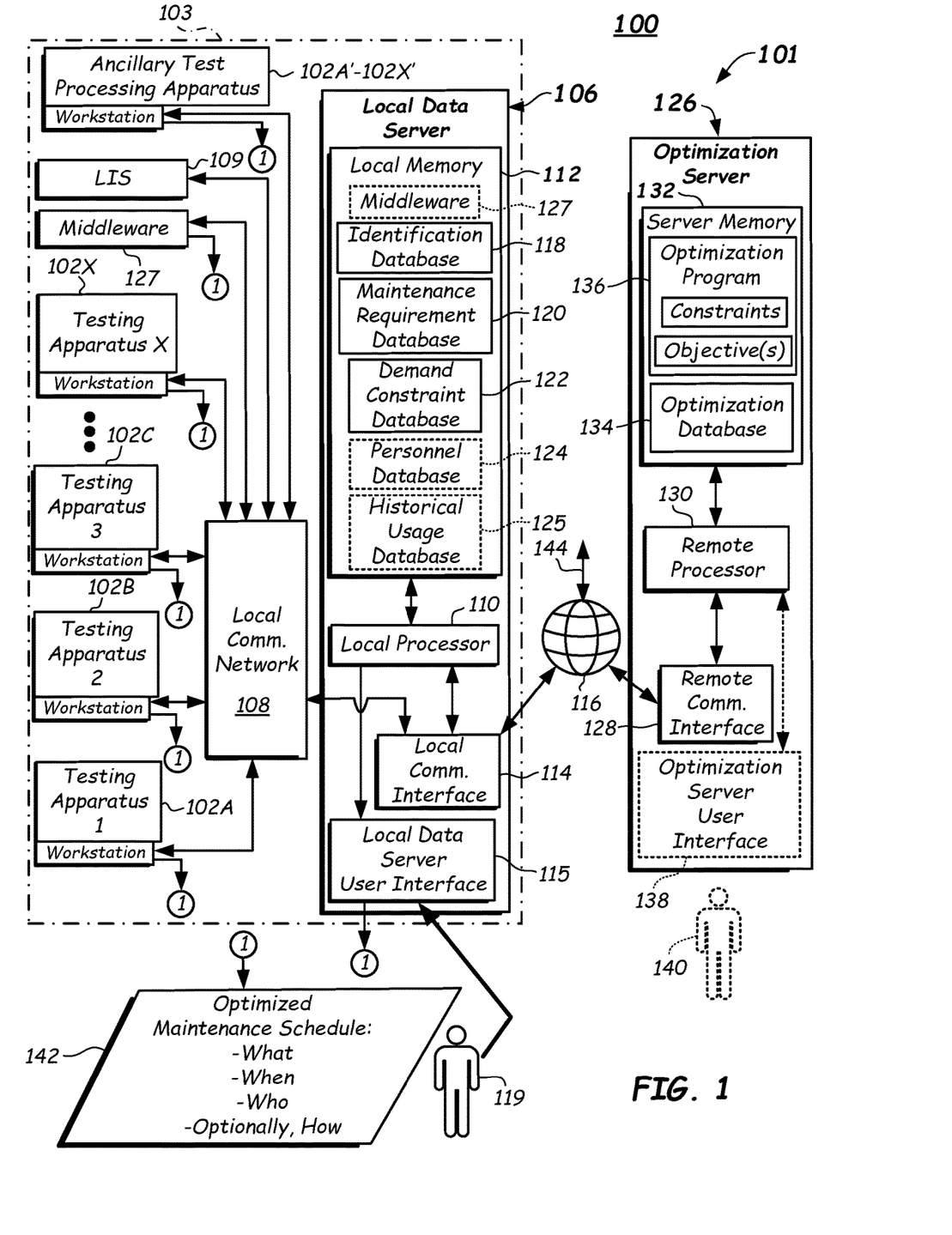
FIG. 1 illustrates a schematic diagram of a maintenance scheduler apparatus configured to provide an optimized maintenance schedule for a plurality of automated testing apparatus, and possibly related ancillary test processing apparatus, according to one or more embodiments of the disclosure.

In accordance with one or more apparatus embodiments described herein, referring to FIG. 1, an automated testing system 100 including a maintenance scheduler apparatus 101 is shown and described. The automated testing system 100 includes a plurality of automated testing apparatus 102A-102X and possibly related ancillary test processing apparatus 102A'-102X', which may be included within a lab 103 (shown dotted). Lab 103 may be one lab or a collection of labs at one facility, for example. The plurality of automated testing apparatus 102A-102X may comprise one or more of a medical diagnostic device (e.g., immunoassay instrument, clinical chemistry analyzer, in vitro analyzer, or the like), and possibly one or more pieces of related ancillary test processing apparatus 102A'-102X' that are ancillary to the immunoassay instrument, clinical chemistry analyzer, in vitro analyzer, or the like, or combinations of any of the afore-mentioned. The ancillary test processing equipment 102A'-102X' can comprise one or more of a centrifuge adapted to fractionate a specimen in a sample container, decapper adapted to remove a cap from a sample container, an aliquoter adapted to aspirate and dispense a specimen and/or reagent to a sample container, a sealer adapted to seal a sample container with aluminum foil, a quality checking module adapted to check for quality of a specimen in a sample container, a vessel mover adapted to move sample containers, a sample handler adapted to move a sample container, a refrigerated storage module, a bulk input module, and the like. In some embodiments, such as in large labs 103, the plurality of automated testing apparatus 102A-102X and possibly ancillary test processing apparatus 102A'-102X' can comprise 10 or more, or even 20 or more, 30 or more, 40 or more, 50 or more, 75 or more, or even 100 or more medical diagnostic devices 102A-102X and ancillary test processing apparatus 102A-102X. In some embodiments, the plurality of automated testing apparatus 102A-102X and related test processing equipment can comprise 200 or more, 300 or more, 400 or more, or even 500 or more automated testing apparatus 102A-102X and ancillary test processing equipment 102A'-102X'.

Various components of the plurality of automated testing apparatus 102A-102X and ancillary test processing equipment 102A'-102X' that may need maintenance may be one or more motors, pumps, probes, aspiration/dispense systems, valves, reservoirs, delivery lines, bearings, mechanical assemblies and devices, moving components, sensors, readers, processors, electronic circuits or electronic components, wires, wiring harnesses, waste compartments or receptacles, and the like.

The automated testing system 100 includes the maintenance scheduler apparatus 101. The maintenance scheduler apparatus 101 can comprise a local data server 106, the local data server 106 including a local processor 110, a local memory 112, and an optimization server 126 configured to communicate with the local data server 106, the optimization server 126 further comprising: a server memory 132 configured to store a compilation of identification data on the plurality of automated testing apparatus 102A-102X and possibly ancillary test processing equipment 102A'-102X' to be maintained, and an optimization program 136 (e.g., a MILP solver) executable on the optimization server 126 to generate an optimized maintenance schedule 142 for the plurality of automated testing apparatus 102A-102X and possibly ancillary test processing equipment 102A'-102X'. Other suitable optimization programs may be used.

The local data server 106 may be in electronic communication with the plurality of automated testing apparatus 102A-102X and possibly ancillary test processing equipment 102A'-102X' in some embodiments. The plurality of automated testing apparatus 102A-102X and possibly ancillary test processing equipment 102A'-102X' may each include a workstation including a suitable microprocessor and memory for controlling the operation of the particular apparatus. Workstations may include a screen display, a keyboard or other input peripheral, and possibly a printer as well.

Electronic communication may be by way of a local communication network 108. For example, the local communication network 108 may be a suitable wired or wireless network, such as a local area network (LAN), wireless local area network (WLAN), power line communication (PLC) network, wide area network (WAM), or the like. Other suitable local communication network types may be used for electronic communication (either wired or wireless).

The local data server 106 may be any suitable computing device including the local processor 110, the local memory 112, and a local communication interface 114. The local data server 106 may also include a local data server user interface 115, which may be a keyboard, printer, display screen or combined screen/keyboard in any form, speaker, or the like that is configured to input various data and/or instructions and/or print, display, or otherwise communicate the optimized maintenance schedule 142 received from the optimization server 126 and which may provide a maintenance window alert for the personnel carrying out the maintenance. The optimized maintenance schedule 142 may be provided on a per lab basis or on a per apparatus basis.

Local communication interface 114 may include any suitable device or collection of devices enabling digital communication with the local communication network 108, such as Ethernet adapter and a router, modem, interface card, or combinations thereof that may enable data communication over the internet 116. Any suitable communication protocol may be used, such as TCP/IP protocol or the like. Data relating to the automated testing apparatus 102A-102X and possibly ancillary test processing equipment 102A'-102X' and optimized maintenance schedule 142 may be stored in the local memory 112 in one or more local databases. In some embodiments, the local communication network 108 may be in electronic communication with a laboratory information system (LIS) 109 to enable the automated testing apparatus 102A-102X to receive test orders and return results thereof to the medical professional ordering the test(s).

For example, stored in local memory 112 may be an identification database 118. Identification database 118 may include identification data (ID) on the plurality of automated testing apparatus 102A-102X and possibly ancillary test processing equipment 102A'-102X' to be maintained. The identification data (ID) can include, but is not limited to, model number or name, serial number, asset number, name, nickname, or other suitable apparatus identifier. The ID can be included in the identification database 118 through input by lab personnel 119, and/or otherwise by electronic communication between the local data server 106 and one or more of the plurality of automated testing apparatus 102A-102X and possibly ancillary test processing equipment 102A'-102X' via local communication network 108.

As used herein, personnel 119 is any person that is responsible for managing, operating, or performing maintenance on the plurality of automated testing apparatus 102A-102X and possibly ancillary test processing equipment 102A'-102X', and this may include outside contractors as personnel 119. In the case of electronic communication, sampling of the plurality of automated testing apparatus 102A-102X and possibly ancillary test processing equipment 102A'-102X' may be taken at any suitable time or interval, such as periodically every minute, every hour, every day, every week, every month, at the start of a shift, or during a shift, upon each startup, or any other suitable time period or at any other suitable milestone. Such sampling may be used to determine the usage patterns of each of the plurality of automated testing apparatus 102A-102X and possibly ancillary test processing equipment 102A'-102X', which may be used as a constraint in the optimization method.

Additionally stored in local memory 112 may be a maintenance requirement database 120. Maintenance requirement database 120 may include maintenance requirement data. Maintenance requirement data may not be a firm requirement in a strict sense, as the optimization may allow deviations from optimal timing or frequency of conducting the maintenance items. The maintenance requirement data may comprise, but may not be limited to, 1) data on what maintenance item (MI) or items (MIs) are to be performed on the plurality of automated testing apparatus and related test processing equipment 102A-102X (which may be identified by a maintenance item number), 2) frequency data of the maintenance item (MI) on the plurality of automated testing apparatus 102A-102X, i.e., how often (at what frequency (F)) the particular maintenance item (MI) is desired to be conducted in either a predefined time period (minutes, hours, shift(s), days, weeks, months, etc.) or number of hours of usage (UH) of the ID, 3) an amount of time the particular maintenance item (MI) will take (e.g., number of hours of maintenance time (MT)), 4) certification requirement data regarding a level of training (Certification Level-CL) required for personnel 119 to have in order to be qualified to perform the maintenance item (MI), cost of various personnel 119.

Additionally stored in local memory 112 may be a demand constraint database 122. Demand constraint database 122 may include demand constraint data. The demand constraint data may comprise, but may not be limited to: 1) personnel availability (AD) data on personnel 119 that can perform maintenance items (MI), and/or 2) apparatus maintenance availability (MA) data for each of the plurality of automated testing apparatus 102A-102X, i.e., what predefined blocks of time (time bins) during a defined period of time can the maintenance item (MI) take place (e.g., 1:00 pm to 6:00 pm).

The availability of personnel 119 (AD) may be provided from a personnel database 124, which may be provided on the local data server 106 or on another data server in electronic communication with the local data server 106. Availability of personnel 119 (AD) may be provided as an input in terms of target hours over the planning period. Optionally, work schedules and target hours for each of the personnel 119 may be manually entered into the demand constraint database 122. In some embodiments, the certification level (CL) of the lab personnel 119 may also be a demand constraint.

In some embodiments, apparatus maintenance availability (MA) data for each of the plurality of automated testing apparatus 102A-102X and possibly ancillary test processing equipment 102A'-102X' can be provided. The apparatus maintenance availability (MA) data can be entered manually or can be provided by communication with one or more of the plurality of automated testing apparatus 102A-102X and possibly ancillary test processing equipment 102A'-102X' via the local communication network 108 or optionally with middleware 127. Middleware 127 may be a software program that aids with scheduling of testing load plans and/or inventory management for at least some of the plurality of automated testing apparatus 102A-102X and possibly ancillary test processing equipment 102A'-102X'. Thus, maintenance availability (MA) can be coordinated with load plans for the plurality of automated testing apparatus 102A-102X and possibly ancillary test processing equipment 102A'-102X' so that certain maintenance items may take place at off peak time bins. Optionally, the plurality of automated testing apparatus 102A-102X and possibly ancillary test processing equipment 102A'-102X' can be considered to always be available for maintenance.

In some embodiments, the optimization method can comprise access to historical usage (HU) data of each of the plurality of automated testing apparatus 102A-102X and may also include HU data possibly ancillary test processing equipment 102A'-102X'. For example, a HU database 125 can include HU data on at least some, or all, of the plurality of automated testing apparatus 102A-102X and possibly ancillary test processing equipment 102A'-102X'. The HU data for at least some of the plurality of automated testing apparatus 102A-102X and possibly related test processing equipment 102A'-102X' can include, but is not limited to, for one or more previous planning periods:
  total usage time (UT),
  total number of tests performed (NT),
  number of tests performed per time bin (TTB),
  identification of time bins with peak usage (PUB),
  total offline time (TOT—when not in use),
  time bins with offline time over the whole bin (OT), and/or
  actual maintenance time (AMT) for undergoing a schedule maintenance item (MI).

In some embodiments, the above-listed HU items can be provided for all of the plurality of automated testing apparatus 102A-102X and related test processing equipment 102A'-102X'. Some or all of the HU data may be recorded for one or more planning periods in the past. Although, HU data can include any other suitable metric over a suitable period of time (e.g., one or more prior planning periods). Identification of time bins with peak usage (PUB) can include one or more than one time bin, or any metric based on the time bins with the peak (highest) usage (PUB), such as a percentage of peak. All or any subset of the above-listed items may be tracked for future use in optimizing maintenance scheduling.

Thus, the local databases in local memory 112 can include and store therein ID, MI, F and possibly one or more of UH, MT, CL, AD, MA, HU (UT, NT, TTB, TOT, OT, and/or AMT).

The automated testing system 100 may further include optimization server 126, which may be a remote server, and which may operate in the cloud in some embodiments, for example. The optimization server 126 may be configured to electronically communicate with the local data server 106. Communication may be via a remote communication interface 128 communicating with local data server 106 through the internet 116 or other suitable vehicle for remote communication, such as cellular communication, for example. Other forms of remote communication may be used. The remote communication interface 128 may be a modem, router, interface card, digital communication card, or any combination thereof that enables electronic data communication over the internet 116 or any other form of remote wired or wireless communication. Any suitable communication protocol may be used, such as TCP/IP protocol, or the like.

Optimization server 126, which may be at a different facility than local data server 106, may receive and store data from the local data server 106 in server memory 132, such as in an optimization database 134. The data received and stored in the in server memory 132 may include the previously-mentioned data on ID, MI, F and possibly one or more of UH, MT, CL, AD, MA, and/or HU (UT, NT, TTB, TOT, OT, and/or AMT). Other suitable associated and/or calculated data, including demand constraints, may be included in the optimization database 134. Like data received and stored in the in server memory 132 from multiple different customers utilizing pluralities of testing apparatus (like pluralities of automated testing apparatus 102A-102X and possibly ancillary test processing apparatus 102A'-102X') may be processed by the optimization server 126. Such processing using the optimization methods described herein can be used to produce an optimized maintenance schedule (like optimized maintenance schedule 142) for one or more of the respective customers. Each respective optimized maintenance schedule for a customer can be communicated to that respective customer via the internet 116 or other suitable wired or wireless communication.

The optimization server 126 may also store therein the optimization program 136, which may be any suitable optimization routine. For example, in some embodiments, the optimization program 134 can be a mixed integer linear programming (MILP) solver. For example, the optimization program 134 can be a MILP solver such as CPLEX available from IBM. Optionally, an open source MILP solver may be used. Other optimization programs or routines, such as non-linear optimization (e.g., smooth nonlinear programming (NPL)), evolutionary computing, simulated annealing, hill climbing, genetic algorithm, flow network algorithm (otherwise referred to as a transportation network), and the like may be used.

The optimization program 136 operates on the data stored in the optimization database 134 and given certain demand constraints and one or more objectives, to be described more fully below, produces an optimized maintenance schedule 142. In particular, the identification data, maintenance requirement data, and demand constraint data can be input and operated on by the optimization program 136, such as an MILP solver or the like, subject to demand constraints and one or more objectives to be optimized executing on the optimization server 126.

The optimization server 126 may also include an optimization server user interface 138, which may be used by a remote operator 140 to set up the optimization problem and help in managing the execution of the optimization method using the optimization program 134.

In more detail, the optimization method using the optimization program 134 can be as follows, for example. Using the optimization method, the problem of maintenance scheduling of the plurality of automated testing apparatus 102A-102X and possibly related test processing equipment 102A'-102X' under resource demand constraints is addressed. In this example optimization method, the real situation of where the plurality of automated testing apparatus 102A-102X and possibly related test processing equipment 102A'-102X' is subject to both periodic and singular maintenance items (e.g., maintenance tasks) during a planning period is considered. The planning period is a period of time over which the maintenance for multiple pieces of equipment is to be scheduled. The planning period can be divided into a number of equal, periodic, predefined time periods (time bins) that can be of any arbitrary duration, such as a number of hours, a shift, a number of shifts, or other suitable time period, depending on the length of time a maintenance item will take, such as on average.

As implemented in this example, the planning period is divided into consecutive, ordered time blocks (time bins) and the various maintenance items (MI) will be assigned into these time blocks (time bins). The demand constraints in this example are resource demand constraints that arise due to the availability (or unavailability) of eligible staff, i.e., the demand constraints are based on personnel availability (AD) data on personnel 119 that are available to perform the maintenance items (MI).

In this example, the optimization method can further include the cost of personnel staffing as an input. One of the optimization goals can be minimizing the maintenance costs while assigning the maintenance items (MI). Costs of personnel 119 are especially relevant when each maintenance call to perform a maintenance item (MI) can be, in some cases, outsourced and can incur a substantial cost.

One assumption of the optimization method is that maintenance staff (personnel 119) that can carry out maintenance items (MI) that are "complex" require a higher certification level (CL) and are subject to a higher pay rate. Their assignment should be reserved only for such maintenance items (MI) that are deemed "complex," and not for maintenance items (MI) that are deemed "rudimentary" and that can be performed by any personnel 119. In this example, the optimization method can also accommodate the case where personnel availability (AD) data of available personnel 119 have "target hours" for the planning period and minimal deviation from these target hours is desired. In this example, the proposed optimization method framework allows the use of a combination of these two staffing-related considerations, i.e., whether complex or rudimentary, as well as personnel availability (AD) data on target hours of available personnel 119.

In this example of the optimization method, the following further assumptions are made about the maintenance items (MI) to be performed:

1. Maintenance items (MI) can be periodic or singular in the given planning period. Both types have an optimal start time under ideal circumstances. For periodic maintenance items (MI), the optimal start time of the first maintenance item (MI) together with the task duration (maintenance time (MT)) and frequency (F) is sufficient to determine the optimal start time of succeeding maintenance items (MIs).

2. Both periodic and singular maintenance items (MIs) can occupy multiple time bins and once a maintenance item (MI) is started it cannot be interrupted.

3. Maintenance items (MIs) cannot be assigned to a personnel 119 if they are not available for the full duration (maintenance time (MT)) of the maintenance item (MI).

4. For a given planning period each personnel 119 can have "target hours" to work based on availability data (AD) of the personnel 119 as determined by, for example, their contract and/or employment type, or work schedule.

5. Certain maintenance items (MIs), such as periodic maintenance items (MIs), have to abide to an order of execution.

6. Each maintenance item (MI) has an eligibility profile that lists the personnel 119 that have the certification level (CL) that is required to perform a particular maintenance item (MI).

7. Maintenance items (MIs) can be performed earlier or later than their optimal timing. This is needed to avoid infeasibility with respect to personnel availability (AD) and eligibility based on certification Level (CL).

8. It is assumed that each maintenance item (MI) requires only one personnel 119 to perform the maintenance item (MI).

Example Optimization Method

As used below "maintenance item (MI)" and "task" are used interchangeably and mean the same thing. In the example optimization method, let $X_{ijk}$ denote a binary decision variable, which indicates the assignment of task $i \in \mathcal{T}$ to personnel $j \in \mathcal{J}$ at time unit $k \in \mathcal{K}$ and $\mathcal{T}$ and $\mathcal{J}$ represent the sets of tasks and personnel and $\mathcal{K} = \{1, 2, 3, , \text{kmax}\}$ represents the ordered planning time line with respect to the chosen time bins.

Furthermore:

$$X_{ijk} = \begin{cases} 1 & \text{if task } i \text{ is assigned to personnel } j \text{ in the } k-th \text{ time unit} \\ 0 & \text{otherwise} \end{cases}$$

Each time bin spans a finite amount time in the planning period and tasks can span more than a unit of these time bins. The duration of task i in terms of time units is denoted as $d_i$ ($d_i$ is equal to maintenance time MT). The optimization method, as stated above, assumes that together with singular jobs, there are multiple periodic jobs. Each periodic job family of maintenance items (MI) is defined by an ordered subset of tasks:

$PJ_1 = \{i, i+1, i+2, \ldots, i+n\}$ from the set $\mathcal{T}$ with frequency $f_i$ (otherwise referred to herein as frequency (F)) defined in terms of the number of time bins.

According to the optimization method, the optimal start time of task i is defined as $o_i$ such that:

$o_i \in \mathcal{K}$

For each singular task the optimal start time has to be provided and for periodic tasks only the optimal start time of the first task is provided. As tasks might not be necessarily performed in their optimal timing, the method defines the following binary variable:

$$y_{ik} = \begin{cases} 1 & \text{if task } i \text{ is started at the } k-th \text{ time unit} \\ 0 & \text{otherwise} \end{cases}$$

According to the optimization method, two non-negative integer variables are defined for each task that measures the deviation from the optimal start time of a task. They are $late_i$ and $erl_i$ corresponding, respectively, to delayed and early executions. The duration of the task is defined as $d_i$ that is expressed in terms of time units.

Further, according to the optimization method, multiple staff-based input variables are defined to be able to encapsulate personnel-specific requirements of particular personnel 119. According to the optimization method, a binary input variable $e_{ijk}$ is used to identify personnel j that can perform work at time unit k, i.e., they are available based on availability data (AD), and further task i lists personnel j as being eligible based on certification level (CL).

Thus, according to the optimization method:

$$e_{ijk} = \begin{cases} 1 & \text{if personnel } j \text{ is available and eligible} \\ & \text{for task } i \text{ at the } k-th \text{ time unit} \\ 0 & \text{otherwise} \end{cases}$$

Thus, for the k-th time unit, the value of $e_{ijk}$ establishes whether j is available and eligible to perform task i. This binary input variable $e_{ijk}$ will be used by the optimization method to prevent assignments that are not feasible in terms of personnel availability (PA) or certification level (CL). The optimization method also associates a "target working duration" in terms of the time bins for each personnel 119 denoted as $t_{j,target}$ and a staffing cost per unit time slot for task i as $C_{ij}$. The optimization and input variables are listed in Table 1 below.

Constraints of Maintenance Scheduling Optimization Method

Herein below, example demand constraints for the example maintenance scheduling method are identified. Further, the demand constraints for the maintenance scheduling method are provided to ensure the resulting assignment of tasks i to personnel 119 satisfy the assumptions listed previously. Other and different demand constraints can be used. Further, each maintenance item (MI) has to be completed with respect to availability and eligibility demand constraints, as follows:

1. Completion of tasks with respect to availability and eligibility. Each task i has to be completed with respect to data on availability and eligibility demand constraints:

$$\Sigma_{j \in} \mathcal{J} \Sigma_{k \in} \mathcal{K} x_{ijk} e_{ijk} = d_i \forall i \in \mathcal{T} \quad (2)$$

2. Moreover, the task i must be completed by a single personnel 119. In formulating this demand constraint, the method can define an indicator function I. The indicator function I can be given as:

$$I: Z_+^{N \times J} \longrightarrow \{0, 1\}^{N \times J}$$

Here $Z_+$ refers to the set of all non-negative integers. The constraint can then be written as:

$$\Sigma_{j \in} \mathcal{J} I\{\Sigma_{k \in} \mathcal{K} x_{ijk}\} = 1 \ \forall i \in \mathcal{T} \quad (3)$$

where the expression $I\{\Sigma_{k \in} \mathcal{K} x_{ijk}\}$ is 1 if personnel j is assigned to task i.

TABLE 1

Variable list involved in the example optimization method.

| Variable Name | Definition | Type |
|---|---|---|
| $x_{ijk}$ | 1 if task i is assigned to personnel j at time unit k | Optimization |

TABLE 1-continued

Variable list involved in the example optimization method.

| Variable Name | Definition | Type |
|---|---|---|
| $y_{ik}$ | 1 if task i starts at time unit k | Optimization |
| $e_{ijk}$ | 1 if staff j is available and certified to perform task i at time unit k | Input |
| $o_i$ | Optimal start time of task i in the planning period, i.e., $o_i \in \mathcal{K}$ | Input |
| $late_i$, $erl_i$ | Non-negative integer slack variables measuring the deviation from $o_i$ corresponding to delayed and early executions. | Optimization |
| $d_i$ | Duration of task i in terms of time bins | Input |
| $f_i$ | Frequency of period task i in terms of time bins | Input |
| $C_{ij}$ | Unit time cost of personnel j to work on task i | Input |
| $t_{j,target}$ | Target work duration of personnel j in terms of time bins in the planning period | Input |
| $t_{j,over}$, $t_{j,under}$ | Slack variables corresponding to over and under deviation from the target working duration of personnel j | Optimization |
| $b_{i,late}$, $b_{i,erl}$ | Upper bounds corresponding the late and early deviations for task i | Input |

3. Concerning the continuity of each task i, the following are provided. These constraints incorporate the start time of the task i and make sure that once a task i is started, task i ends without interruption:

$$\Sigma_{j \in} \mathcal{J} x_{ijk} = \Sigma_{l=max(1, k-d_i+1)} y_{il} \forall i \in \mathcal{T} \text{ and } \forall k \in \mathcal{K} \quad (4)$$

This equation (4) above ensures that if $x_{ijk}=1$ then $y_{ik}$ has to be 1 within the duration of the task i, as it must have started.

The following further constraint ensures that tasks finish without interruption:

$$\sum_{l=1}^{k_{max}-d_i+1} y_{il} = 1 \forall \ i \in \mathcal{T} \quad (5)$$

Then the actual start time is related to the optimal start time as follows:

$$o_i - erl_i + late_i = \Sigma_{k \in} \mathcal{K} \ y_{ik} k \forall i \in \mathcal{T} \quad (6)$$

4. Concerning the order of task constraints: These constraints enforce that task order is maintained between any two tasks:

$$x_{ajk} \geq x_{bjk} \ \forall k \in \mathcal{K}, j \in \mathcal{J} \text{ if task a must precede task b} \quad (7)$$

These constraints have to be enforced between every consecutive task pair in a family of periodic jobs. In general, such constraints can be enforced between singular tasks or between singular tasks or periodic tasks, as necessary.

5. Optimal start time constraints for periodic jobs: The optimal start time of a task in a family of periodic jobs is dictated by the start time of the preceding task (unless it is the first task in the family):

$$o_{i+1} = o_i - erl_i + late_i + d_i + f_i, \ \forall (i, i+1) \in PJ_l \quad (8)$$

The start time of the preceding task is measured by $o_i - erl_i + late_i$ and given this, the optimal start time of the next task can be obtained by the above equation.

6. Each personnel should be as close to their target work time as possible: In defining these constraints we define non-negative slack variables measuring over and under time: $t_{j,over}$ $t_{j,under}$. Then the following constraints can be written for each personnel 119:

$$\Sigma_{i \in} \mathcal{K} \Sigma_{k \in} \mathcal{K} x_{ijk} - t_{j,over} + t_{j,under} = t_{j,target} \forall j \in \mathcal{J} \qquad (9)$$

In these demand constraints, we measure the working time and the corresponding slack variables in terms of the time bins. However, it is trivial to associate each time bin with an actual duration of time (and possibly varying) and directly measure the working hours.

7. Enforcing no latency or early work for certain tasks: Although it might not be possible to perform every task on time there might be a certain task that needs to be completed always on time, or never late but can be completed early or never early but can be completed late. In another case, late and early deviations can be bounded. The framework of the example optimization method can handle these cases as follows:

(a) $erl_i = 0$ and $late_i = 0$ for $i \in \mathcal{T}$ that has to be completed on time.
(b) $erl_i = 0$ for $i \in \mathcal{T}$ that cannot be started early.
(c) $late_i = 0$ for $i \in \mathcal{T}$ that cannot be started late.
(d) $late_i \leq b_{i,late}$ for $i \in \mathcal{T}$ that has a bounded late deviation.
(e) $erl_i \leq b_{i,erl}$ for $i \in \mathcal{T}$ that has a bounded early deviation.

As discussed previously, enforcing exact completion time can cause infeasibilities in the optimization method when there is no available and eligible personnel 119 to perform the task i. Similarly, enforcing no-late, no-early, or bounded deviation constraints can cause infeasibilities and hence must be enforced carefully. The proposed framework of the example optimization method can utilize any combination of these constraints for the tasks i to be assigned. Other suitable demand constraints could be used.

Objectives of Maintenance Scheduling Optimization Method

In the example optimization method, one or several objectives can be sought to be optimized. If more than one, these objectives can be weighted or otherwise ordered, as desired, to emphasize one objective over another. The objectives can be minimization of one or more of deviation from optimal maintenance times, minimization of total cost, and/or minimization of deviation from target work duration. Other suitable optimization goal(s) may be used, such as optimum use of down time or low usage time for maintenance items. More or less numbers of optimization goals may be sought to be optimized.

In more detail, the example objectives can be:
1. Minimization of Deviation from Optimal Maintenance Times:

$$\mathcal{O}_{time} = \Sigma_{i \in} \mathcal{T} \lambda_i g_{i,erl}(erl_i) + \Sigma_{i \in} \mathcal{T} \beta_i g_{i,late}(late) \qquad (10)$$

This cost function minimizes the total cost of tasks not being completed on time. In this formulation for each slack variable we use a function: $g_{i,-}$. When these functions are picked to be linear such that $g_{i,-}(s) = s$, then the cost function is indifferent to the distribution of magnitudes of variables as long as the total cost remains the same. This can potentially cause some tasks to have large deviations. Ideally, if it is not possible to perform tasks on time, it can be more preferable to have each task similar amount of deviation. This can be achieved by choosing $g_{i,-}(s) = s^2$. However, using a quadratic function can create computational challenges that can be alleviated by using a piecewise-linear function that can be defined through its breakpoints. If the breakpoints are chosen appropriately (such as to mimic a quadratic), this approach can achieve a balanced deviation from optimal start times without the computational burden. We also employ $\lambda i$ and $\beta i$ to individually weigh each cost term as needed. The use of such weights is relevant when one case, such as being early, is preferable to being delayed.

2. Minimization of Total Cost:

$$\mathcal{O}_{cost} = \Sigma_{i \in} \mathcal{T} \Sigma_{j \in} \mathcal{J} c_{ij}(\Sigma_{k \in} \mathcal{K} x_{ijk}) \qquad (11)$$

Here the optimization method measures the cost of the total assignments of the tasks. This objective can be relevant especially when each maintenance call to perform a maintenance item (MI) may be outsourced. By optimizing such a cost objective we make sure that personnel 119 with higher pay rates are assigned to tasks only if it is not possible to fulfill the task with a personnel at a lower pay rate.

3. Minimization of Deviation from Target Work Duration:

$$\mathcal{O}_{staff} = \Sigma_{j \in} \mathcal{J} \gamma_j h_{j,over}(t_{j,over}) + \Sigma_{j \in} \mathcal{J} \eta_j h_{j,under}(t_{j,under}) \qquad (12)$$

This objective of the method aims at minimizing the deviation from target working duration for each personnel 119, so as to minimize overtime hours. Similar to the deviation of optimal maintenance times, a distribution aware transform $h_{j,-}$ can be used to achieve balanced deviations from target working durations. Similarly, $\gamma_1$ and $\eta_j$ can be used to individually weigh each cost term.

The framework of the method has three cost functions that aim at optimizing different aspects of maintenance scheduling. Therefore, it is up to the needs of the end-user to prioritize between these objectives. The user can either determine an ordering of the objectives, which can be translated to lexicographic optimization or can appropriately weigh the objectives:

$$\mathcal{O}_{total} = w_1 \mathcal{O}_{time} + w_2 \mathcal{O}_{cost} + w_3 \mathcal{O}_{staff} \qquad (13)$$

where $w_1, w_2, w_3 \in \mathcal{R}^+$.

Once the optimized maintenance schedule 142 is generated, the schedule can be communicated by any suitable mechanism, such as through the internet 116, to the local data server 106, or elsewhere. The communication may be through the data server user interface 115 in one example. The optimized maintenance schedule 142 may be provided through a visual display (e.g., displayed on a visual display monitor/screen) to the local lab personnel 119. Optionally, the optimized maintenance schedule 142 may be provided as a printout to be used by the local lab personnel 119. In another embodiment, the maintenance schedule 142 can be provided in a format comprising a data file. For example, the data file can be provided as an input to an electronic calendar of the local personnel 119 or personnel 119 that are contracted for.

Optionally or additionally, if personnel 119 qualified to perform the maintenance are not present at the lab 103, then a service call (e.g., service ticket) may be initiated to an instrument manufacture or servicer (e.g., contractor), wherein a service technician personnel 119 is commanded to be sent to the location of the instrument 102A-102X to perform the scheduled maintenance.

In some embodiments, the local communication network 108 can be configured to electronically communicate the optimized maintenance schedule 142 to one or more of the plurality of automated testing apparatus 102A-102X or ancillary test processing apparatus 102A'-102X'. Thus, a workstation at one or more of the plurality of automated testing apparatus 102A-102X or ancillary test processing apparatus 102A'-102X' can be configured to communicate the optimized maintenance schedule 142 to the local lab personnel 119 or other personnel 119 performing the schedule maintenance for that automated testing apparatus 102A-102X or ancillary test processing apparatus 102A'-102X'.

In another embodiment, the local communication network 108 can be configured to electronically communicate the optimized maintenance schedule 142 to middleware 127. Middleware 127 can be stored in memory of, and executable on a processor of, another data server coupled to the local communication network 108, for example. Optionally, middleware 127 may be present on the local data server 106.

Another lab(s) (not shown) associated with one or more other local data server(s) (not shown) may also provide data through the internet 116 (as indicated by arrow 144) to remote communication interface 128 so as to be able to perform the optimization method for the other lab(s) and provide an optimized maintenance schedule(s) to the other lab(s), as well. Availability of contracted personnel 119 may be taken into account over multiple customers.

Figure 2:
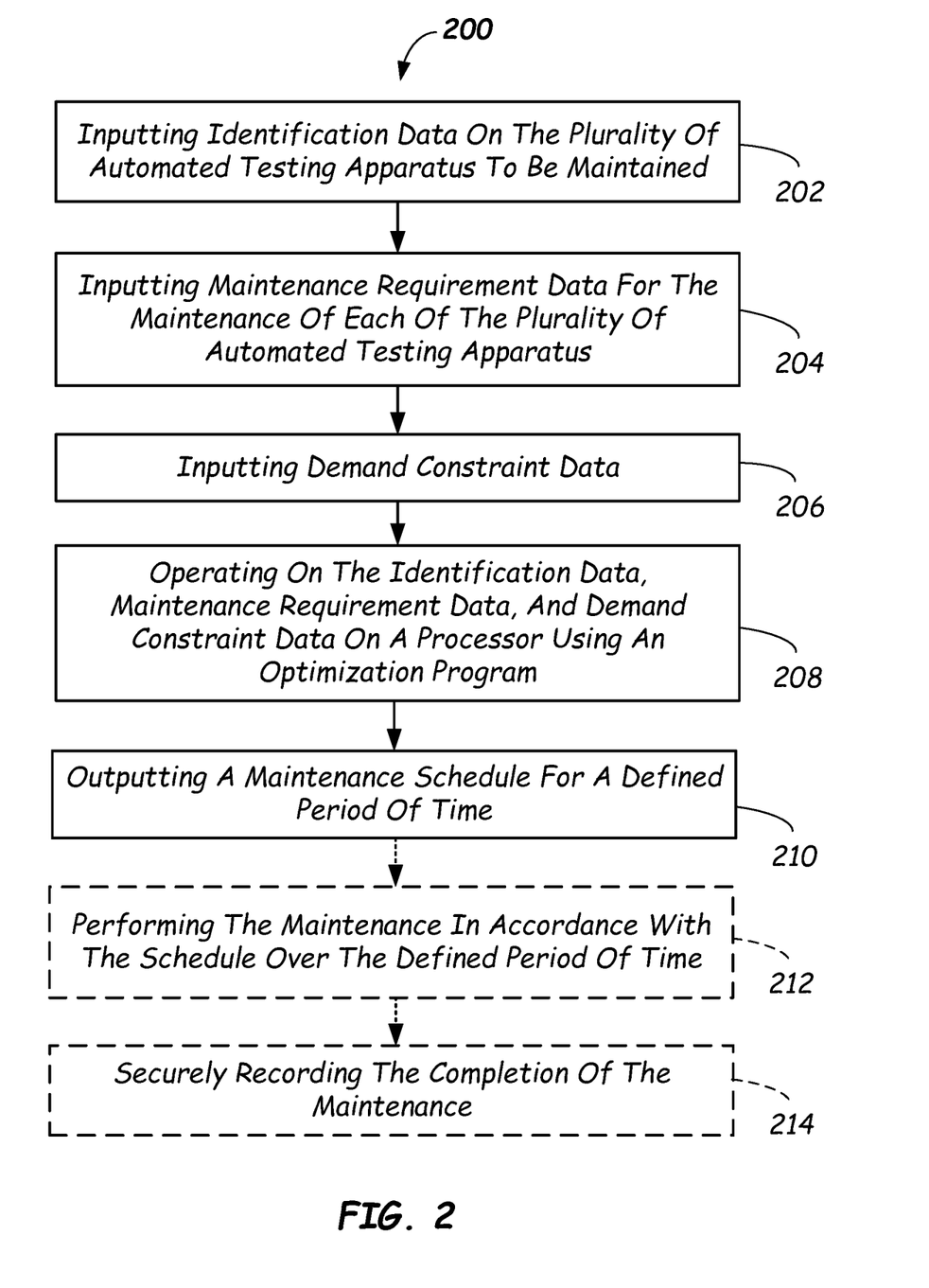
FIG. 2 illustrates a flowchart of a method of scheduling maintenance on a plurality of automated testing apparatus, possibly combined with related ancillary test processing apparatus, according one or more embodiments to embodiments.

In accordance with another embodiment of the disclosure, and as best shown in FIG. 2, a method 200 of scheduling maintenance on a plurality of automated testing apparatus (e.g., automated testing apparatus 102A-102X) and possibly ancillary test processing apparatus (e.g., ancillary test processing apparatus 102A'-102X') is provided. The method 200 comprises, in 202, inputting identification data on the plurality of plurality of automated testing apparatus to be maintained (into the identification database 118, for example), and also possibly on ancillary test processing apparatus (e.g., ancillary test processing apparatus 102A'-102X'). Identification data can include, but is not limited to, model number or name, serial number, asset number, nickname, or other suitable apparatus identifier. The identification data can be entered manually or through electronic communication with at least some of the plurality of automated testing apparatus (e.g., automated testing apparatus 102A-102X) and possibly ancillary test processing apparatus (e.g., ancillary test processing apparatus 102A'-102X') over the local communication network 108.

The method 200 further includes, in 204, inputting maintenance requirement data for the maintenance of each of the plurality of automated testing apparatus (e.g., test apparatus 102A-102X or a subset thereof), and possibly ancillary test processing apparatus (e.g., ancillary test processing apparatus 102A'-102X'). The maintenance requirement data can include: 1) data on what maintenance item (MI) or items (MIs) are to be performed on the plurality of automated testing apparatus (e.g., test apparatus 102A-102X), 2) frequency (F) data of how often the particular MI is required in either a) a predefined time period (hours, shift(s), days, weeks, months, etc.), or b) a number of hours of usage (UH), 3) a number of hours of maintenance time (MT) the MI will take, and/or 4) a level of training (CL) required, or the like.

The method 200 further includes, in 206, inputting demand constraint data. Demand constraint data may comprise, but may not be limited to, 1) availability data (AD) on personnel 119 and/or 2) data on apparatus maintenance availability (MA) for each of the plurality of automated testing apparatus (e.g., automated testing apparatus 102A-102X) and possibly ancillary test processing apparatus (e.g., ancillary test processing apparatus 102A'-102X'), i.e., what predefined blocks of time during a defined period of time can the maintenance item (MI) take place (e.g., 1:00 pm to 6:00 pm). The inputting can be through use of the local data server user interface 115 or through communication with the personnel database 124 and/or the historical usage database 125.

The method 200 further includes, in 208, operating on the identification data, maintenance requirement data, and demand constraint data on a processor (e.g., remote processor 130) using an optimization program (e.g., optimization program 136 such as an MILP solver). Other suitable optimization programs may be used, such as non-linear optimization (e.g., smooth nonlinear programming (NPL)), evolutionary computing, and the like. In the optimization program 136, a mathematical model is constructed defining the demand constraints and one or more optimization goals along with the payload data (e.g., identification data, maintenance requirement data) are then fed to an optimization program 136, such as solver (e.g., MILP solver such as CPLEX). Upon convergence, the optimized results are produced (i.e. the optimized maintenance schedule 142). In some embodiments, where more than one optimization objective (goal) is sought, a weighted optimization may be used, wherein weights can be applied to the relative importance of the objective.

The method 200 further includes, in 210, outputting a maintenance schedule (e.g., the optimized maintenance schedule 142), which is the converged result for the optimization for a defined period of time (the planning period). The defined period of time can be a shift, multiple shifts, a day, a week, a month, or other suitable planning period, for example. Maintenance schedules over other suitable increments of time may be used. The method 200 may further include, in 212, performing the scheduled maintenance items MI in accordance with the maintenance schedule 142 over the defined period of time (planning period) by a suitably-certified personnel 119. Once the maintenance item MI is completed, the completion thereof can be securely recorded in block 214 by any suitable secure means.

The maintenance schedule (e.g., maintenance schedule 142) for the defined period of time can comprise, for example, a type of the maintenance (e.g., by MI) to perform on each of the plurality of automated testing apparatus 102A-102X, and possibly also on the ancillary test processing apparatus (e.g., ancillary test processing apparatus 102A'-102X'), over the defined period of time (the planning period), who (by personnel name or other identification) is to perform the maintenance, and when to perform the maintenance. The maintenance schedule 142 for the defined period can also include instructions or internet or other links to instructions on how the maintenance is to be conducted. For example, a hyperlink to maintenance instructions for the particular scheduled maintenance item MI may be provided on a display screen or the maintenance instructions may otherwise be communicated (such as by a printout or audio or visual instructions). The circled numeral ones in FIG. 1 illustrate the various locations that the optimized maintenance schedule 142 can be communicated.

The optimized maintenance schedule 142 may be optimized in terms of when each of the plurality of automated testing apparatus 102A-102X, and possibly also the ancillary test processing apparatus (e.g., ancillary test processing apparatus 102A'-102X'), should be maintained, how often each of the plurality of automated testing apparatus 102A-102X and possibly the ancillary test processing apparatus (e.g., ancillary test processing apparatus 102A'-102X'), should be maintained, and/or what personnel 119 should maintain each of the plurality of automated testing apparatus 102A-102X and possibly also the ancillary test processing apparatus (e.g., ancillary test processing apparatus 102A'-102X'), and/or for minimizing overall cost of the maintenance over the planning period. Other optimization objectives may be provided, such as maximizing uptime of the plurality of automated testing apparatus 102A-102X and possibly also the ancillary test processing apparatus (e.g., ancillary test processing apparatus 102A'-102X').

In some embodiments, once the optimized maintenance schedule 142 is produced, the personnel 119 can be prompted to complete the maintenance item MI, such as by receiving a suitable prompt. For example, the prompt may be provided at the applicable workstation, for example. If the maintenance is to be performed by personnel 119 that is a contractor, then they may receive a prompt by way of email, text, calendar entry, or other suitable prompt. After the personnel 119 have completed the maintenance item (MI), the personnel 119 can initiate a response to the prompt, or otherwise suitably respond within the maintenance scheduling apparatus 101 so as to record that the maintenance item MI has been successfully completed. Along with the confirmation that the maintenance item has been completed, the local memory 112 can store confirmation data such as a date and/or time stamp of completion of the maintenance item MI, identification of the personnel 119 performing the maintenance item MI on the testing apparatus 102A-102X or ancillary test processing apparatus 102A'-102X', and possibly other pertinent information such as the certification level CL of the personnel 119, the actual time to complete the maintenance item MI, and/or notes to update any instructions or links on how to conduct the maintenance item MI.

The recordation of the confirmation and confirmation data can be accomplished in any suitable digitally-secure manner, such as in block 214. For example, the confirmation data may be promptly sent to the remote server 126 and stored in the server memory 132 thereof. In this manner, a secure digital record of the completion of the maintenance item MI can be stored at another location as proof that the maintenance item was actually completed. Storage on multiple servers with appropriate access control can further secure recordation of the confirmation data.

Optionally, or additionally, confirmation data may be supplied to a third party, such as a regulatory body. The supplying can be with the use of a consensually-shared database, such as a distributed ledger, providing verifiable trust that the confirmation data has been unaltered. A distributed ledger is a database that is consensually shared and synchronized across multiple websites, storage facilities (e.g., cloud) institutions, or geographies. It allows transactions such as the recordation of the completion of the maintenance item. MI to have public witnesses thereby rendering the record more secure and making a cyber-attack more difficult.

While specific apparatus and methods have been shown by way of example embodiments herein, it should be understood that other and different embodiments are possible. It is intended that the disclosure is to cover all modifications, equivalents, and alternatives falling within the scope of the claims.

What is claimed is:

1. A method of scheduling maintenance on a plurality of automated testing apparatus, comprising:
   receiving identification data on the plurality of automated testing apparatus to be maintained;
   receiving maintenance requirement data for maintenance of at least one of the plurality of automated testing apparatus, the maintenance requirement data indicating a maintenance item to be performed;
   receiving demand constraint data, the demand constraint data indicating whether the maintenance item needs to be performed always on time, whether the maintenance item can be performed early or never early, and whether the maintenance item can be performed late or never late;
   operating on the identification data, the maintenance requirement data, and the demand constraint data on a processor using an optimization program subject to the demand constraint data and at least one objective comprising minimization of total maintenance cost to generate a maintenance schedule for a defined period of time; and
   outputting the maintenance schedule.

2. The method of claim 1, further comprising:
   receiving identification data on ancillary test processing apparatus to be maintained that is ancillary to the plurality of automated testing apparatus; and
   receiving maintenance requirement data of the ancillary test processing apparatus.

3. The method of claim 1, wherein the optimization program comprises mixed integer linear programming.

4. The method of claim 1, wherein the identification data comprises model, serial number, asset number, nickname, or other device identifier.

5. The method of claim 1, wherein the plurality of automated testing apparatus comprises one or more immunoassay instruments, one or more clinical chemistry analyzers, or combinations thereof.

6. The method of claim 1, wherein the plurality of automated testing apparatus comprises twenty or more medical diagnostic devices.

7. The method of claim 1, wherein the maintenance schedule is a result of optimizing several objectives.

8. The method of claim 7, wherein the several objectives are weighted or ordered to emphasize one objective over another.

9. The method of claim 1, wherein the at least one objective further comprises:
   minimization of deviation from optimal maintenance times, or
   minimization of deviation from target work duration of personnel carrying out the maintenance.

10. The method of claim 1, wherein the maintenance requirement data comprises:
    data on what maintenance item is to be performed on the plurality of automated testing apparatus,
    frequency data of the maintenance item on the plurality of automated testing apparatus,
    an amount of time the maintenance will take; and
    certification requirement data for personnel who are performing the maintenance item.

11. The method of claim 1, wherein the maintenance requirement data comprises data on the plurality of automated testing apparatus that are subject to both periodic and singular maintenance items during a planning period.

12. The method of claim 1, wherein the demand constraint data comprises:
    personnel availability data.

13. The method of claim 1, wherein the demand constraint data comprises:
    apparatus maintenance availability data for each of the plurality of automated testing apparatus.

14. The method of claim 1, wherein the demand constraint data comprises:
    historical usage data for at least some of the plurality of automated testing apparatus.

15. The method of claim 1, wherein the identification data, maintenance requirement data, and demand constraint data are communicated to an optimization server over an internet.

16. The method of claim 1, wherein the operating on the identification data, maintenance requirement data, and demand constraint data is performed by the optimization program comprising mixed integer linear programming executing on a remote optimization server.

17. The method of claim 1, wherein the outputting of the maintenance schedule for the defined period of time comprises:
a type of the maintenance to perform on the at least one of the plurality of automated testing apparatus over the defined period of time,
who is to perform the maintenance, and
when to perform the maintenance.

18. The method of claim 1, wherein the outputting of the maintenance schedule for the defined period of time comprises instructions on how the maintenance is to be conducted.

19. The method of claim 1, wherein the defined period of time comprises a shift, multiple shifts, a day, a week, or a month.

20. The method of claim 1, wherein the maintenance schedule is provided in a format comprising a printout, a data file, or a screen display.

21. The method of claim 1, further comprising securely storing confirmation data concerning a maintenance item that has been completed.

22. The method of claim 21, wherein the confirmation data comprises a date and time stamp of completion, and identification of the personnel performing the maintenance item on the testing apparatus or ancillary test processing apparatus.

23. A maintenance scheduler apparatus, comprising:
a local data server including:
local memory configured to store an identification database, a maintenance requirement database, and a demand constraint database;
an optimization server configured to communicate with the local data server, the optimization server comprising:
a server memory configured to store:
a compilation of identification data on a plurality of automated testing apparatus to be maintained, maintenance requirement data for maintenance of at least one of the plurality of automated testing apparatus, and demand constraint data in an optimization database, the maintenance requirement data indicating a maintenance item to be performed, and the demand constraint data indicating whether the maintenance item needs to be performed always on time, whether the maintenance item can be performed early or never early, and whether the maintenance item can be performed late or never late; and
an optimization program executable on the optimization server subject to the demand constraint data and at least one objective comprising minimization of total maintenance cost to generate an optimized maintenance schedule for the plurality of automated testing apparatus.

24. The maintenance scheduler apparatus of claim 23, wherein the server memory further comprises:
a compilation of identification data, maintenance requirement data, and demand constraint data on test processing equipment that is ancillary to the plurality of automated testing apparatus to be maintained.

25. The maintenance scheduler apparatus of claim 23, wherein the optimization program executable on the optimization server comprises mixed integer linear programming.

26. A method of scheduling maintenance on a plurality of automated testing apparatus, comprising:
receiving into an identification database in local memory of a local data server, identification data on the plurality of automated testing apparatus to be maintained, wherein the identification data comprises model, serial number, asset number, or other identifier;
receiving into a maintenance requirement database in local memory of the local data server, maintenance requirement data for maintenance of each of the plurality of automated testing apparatus, wherein the maintenance requirement data comprises:
data on what maintenance item is to be performed on the plurality of automated testing apparatus,
frequency data of the maintenance item on the plurality of automated testing apparatus, and
certification requirement data for personnel who are to perform the maintenance item;
receiving demand constraint data into a demand constraints database in local memory of the local data server, the demand constraint data comprising personnel availability data and indicating whether the maintenance item needs to be performed always on time, whether the maintenance item can be performed early or never early, and whether the maintenance item can be performed late or never late;
communicating the identification data, the maintenance requirement data, and the demand constraint data to an optimization server;
operating on the identification data, the maintenance requirement data, and the demand constraint data on the optimization server using an optimization program comprising mixed integer linear programming subject to the demand constraint data and at least one objective comprising minimization of total maintenance cost;
outputting from the optimization server to the local data server an optimized maintenance schedule for a defined period of time based on the operating; and
outputting the optimized maintenance schedule from one or more of a local data server, from one or more of the plurality of automated testing apparatus, or from middleware.

* * * * *

UNITED STATES PATENT AND TRADEMARK OFFICE
CERTIFICATE OF CORRECTION

| | |
|---|---|
| PATENT NO. | : 11,715,559 B2 |
| APPLICATION NO. | : 17/597421 |
| DATED | : August 1, 2023 |
| INVENTOR(S) | : Sandeep M. Naik et al. |

It is certified that error appears in the above-identified patent and that said Letters Patent is hereby corrected as shown below:

On the Title Page

Item (72), delete the first name of the second inventor "Micheal" and replace it with --Michael--

Signed and Sealed this
Twenty-first Day of November, 2023

*Katherine Kelly Vidal*

Katherine Kelly Vidal
*Director of the United States Patent and Trademark Office*